United States Patent [19]
Tillich

[11] Patent Number: 5,441,638
[45] Date of Patent: Aug. 15, 1995

[54] APPARATUS FOR SEPARATING PARTICLES SUSPENDED IN A FLOWING LIQUID

[76] Inventor: Dirk Tillich, Gutshof 2A, D-3305 Lucklum, Germany

[21] Appl. No.: 72,576

[22] Filed: Jun. 4, 1993

[30] Foreign Application Priority Data

Jun. 4, 1992 [DE] Germany .............. 42 18 379.0

[51] Int. Cl.⁶ .................................................. B01D 35/02
[52] U.S. Cl. ................................... 210/242.1; 210/320; 210/411; 210/170; 73/863.21; 73/863.24
[58] Field of Search .................... 210/153–155, 210/162, 170, 242.1, 320, 411, 522, 767, 801, 802; 95/267, 272; 55/442, 445; 73/863.21, 863.22, 863.23, 863.24, 170.29, 170.33

[56] References Cited

U.S. PATENT DOCUMENTS

| | | | |
|---|---|---|---|
| 408,285 | 8/1889 | Boehning | 55/442 |
| 2,314,977 | 3/1943 | Green | 210/522 |
| 2,570,304 | 10/1951 | Bach | 210/802 |

Primary Examiner—Matthew O. Savage
Attorney, Agent, or Firm—Cohen, Pontani, Lieberman, Pavane

[57] ABSTRACT

The disclosure relates to a method and an apparatus for separating particles suspended in a flowing liquid for cleaning a current component. The apparatus has a body that can be submerged below the surface of the flowing liquid. The body is hollow and has at least one outlet for the liquid to exit or be removed through, its upstream end is connected to its downstream end by an essentially smooth shaft, the downstream end is to some extent surrounded by a series of baffles, having a gap between each baffle and there are intakes into the body in the shaft between the baffles. The flow is diverted and reversed below the surface of the fluid such as to produce a zone of turbulence around an extensively quiescent center, whereby the turbulence allows the heavier and more inert particles to travel on, while a current component of lighter-weight molecules with few or no particles and accordingly cleaner continuously enters the quiescent center, where it can be analyzed or continuously extracted outside the system.

9 Claims, 2 Drawing Sheets

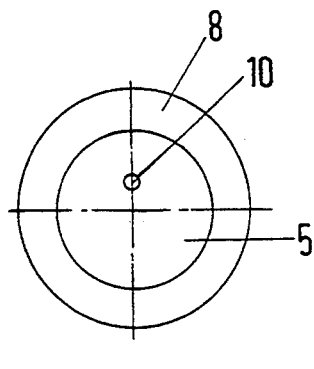
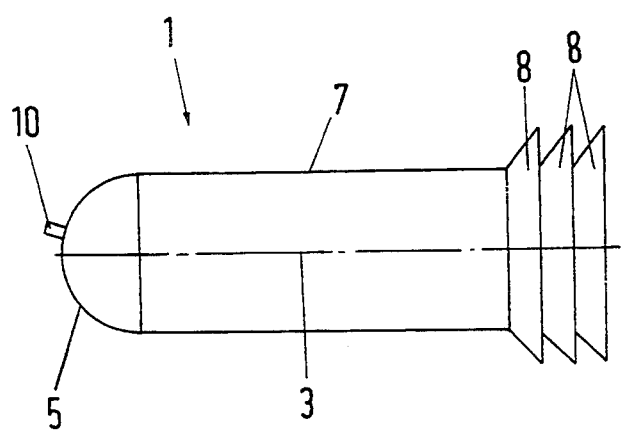
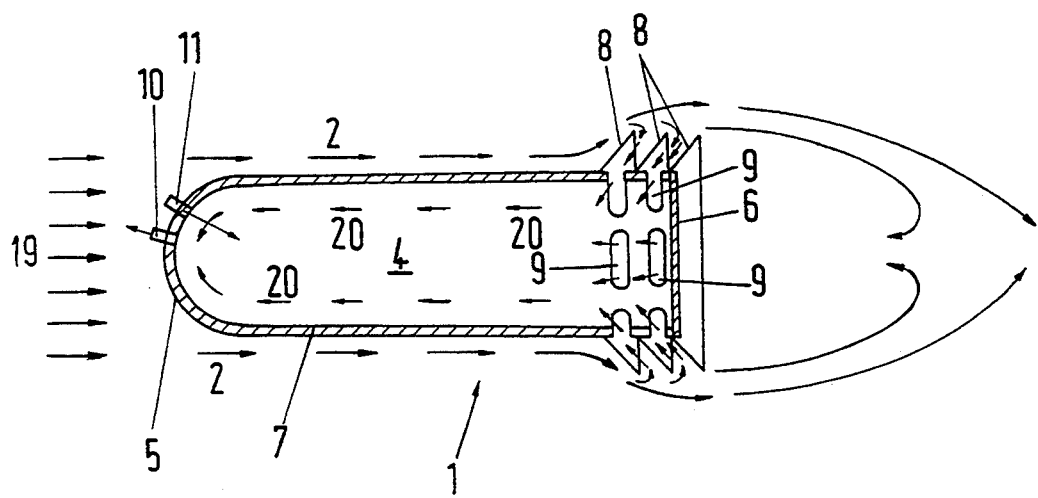

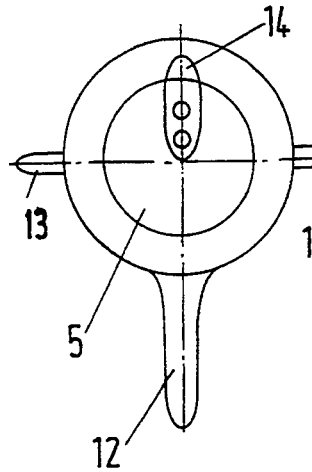
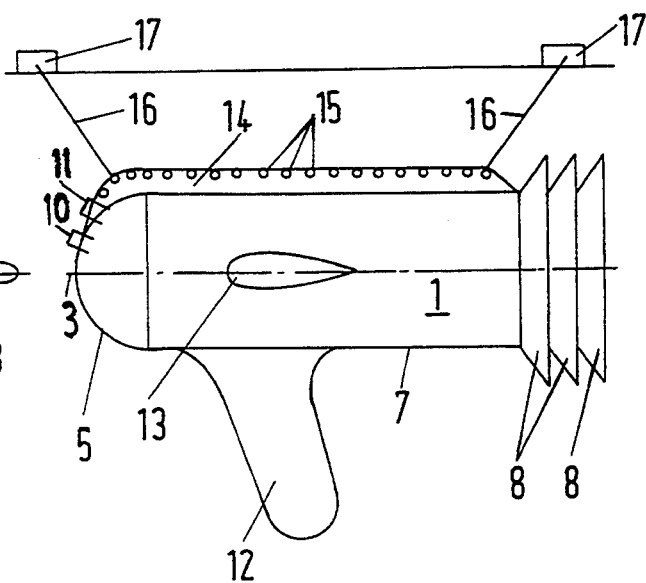
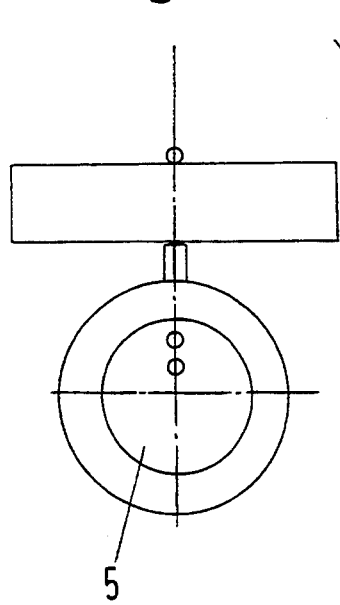
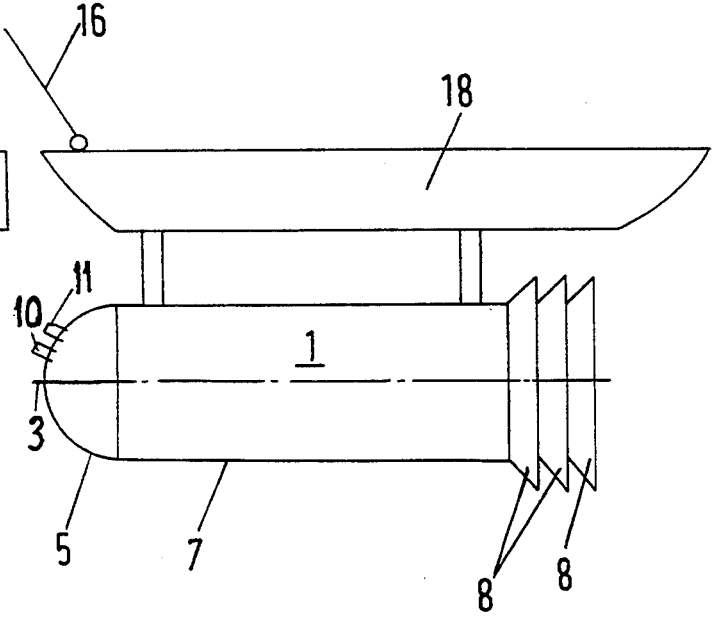

APPARATUS FOR SEPARATING PARTICLES SUSPENDED IN A FLOWING LIQUID

BACKGROUND OF THE INVENTION

The present invention concerns both a method of and apparatus for separating particles suspended in a flowing liquid to obtain a clean current component, one, that is, with few or no particles suspended in it.

There are many applications, especially in the field of materials analysis that require eliminating contaminants in the form of suspended particles from flowing liquids to obtain a clean sample. Filters of woven or ceramic materials have been mostly employed for this purpose until now. A filter separates solids of particular dimensions, which deposits on its surface. The pores rapidly clog up, however, and allow less and less of the clean liquid through. Filters accordingly rapidly become unusable and must be replaced or at least rinsed out fairly often.

Other known methods of separation exploit gravity to separate the heavier solid particles from the lighter molecules of a liquid. This approach, however, requires a still liquid, and an amount has to be removed from the flowing liquid and allowed to come to rest in order to allow the suspended particles to precipitate. A continuous removal of cleaned liquid is, accordingly, impossible.

FIELD OF THE INVENTION

The objects of the present invention are a method of and apparatus for separating particles suspended in a flowing liquid to obtain a clean current component, one, that is, with few or no particles suspended in it.

This object is attained in the method in accordance with the invention by diverting and reversing the flow below the surface of the fluid such as to produce a zone of turbulence around an extensively quiescent center. The turbulence allows the heavier and more inert particles to travel on. A current component of lighter-weight molecules with few or no particles and accordingly cleaner continuously enters the quiescent center. The cleaner component can be analyzed at the center or continuously extracted therefrom for analysis outside the system.

The object is attained in the apparatus in accordance with the invention in that it constitutes a body that can be submerged below the surface of the flowing liquid. The body is hollow and has at least one outlet for the liquid to exit or be removed through. Its upstream end is connected to its downstream end by an essentially smooth shaft. The downstream end is to some extent surrounded by a series of baffles. There is a gap between each baffle and the one next to it. There are intakes into the body in the shaft between the baffles.

SUMMARY OF THE INVENTION

The method and apparatus in accordance with the invention together make it possible to continuously divert a current with few or no particles suspended in it from a current with many particles suspended in it to obtain a sample for analysis, for example. One essential characteristic of the invention is the intentionally produced turbulence that constantly precipitates the sample current of lighter-weight molecules out of the main, particle-laden, current and into the quiescent zone where, extensively cleaned of suspended particles, it can be directly analyzed or whence it can be extracted for analysis outside the system.

The inside of the body in accordance with the invention is free to function as the quiescent center, temporarily accommodating the clean sample current. Analyses can easily be carried out directly inside the body. The body can also accommodate filtering and/or pumping equipment.

To control the flow upstream of the turbulence it is practical for the body to be a surface of rotation with its axis of rotation paralleling the current.

The effectiveness in accordance with the invention of separating the lighter molecules from the heavier particles can be further exploited if the baffles are shaped like skirts extending all around the body and taper radially in toward its downstream end from their outer edge.

Since even the apparatus in accordance with the invention cannot remove all particles from the sample, deposits inside the body cannot be avoided, especially after long use. It will accordingly be of advantage for the body to have a connection for a line to a flushing device.

The body in accordance with the invention cannot function unexceptionably without being positioned precisely within the flowing liquid. It is accordingly of advantage for the body to have stabilizing fins or similar structures on its outer surface in the form of a keel that extends straight down and/or flukes that extend straight out to each side. It will also help to position the body if it has a suspension rack with various points of attachment distributed along it. In this event the body can be attached by a line attached to whatever point will best ensure at least approximate horizontality of the body's axis of rotation within the current in accordance with the prevailing flow conditions.

The lines that attach the body can be anchored to the bed of the channel or secured to anchored buoys or fixed points on shore.

To keep the body stable even when the overall system is temporarily down or when the current is very sluggish, it is practical for it to be attached to and preferably suspended from a floating structure.

Further characteristics of the invention are recited in the subsidiary claims.

BRIEF DESCRIPTION OF THE DRAWINGS

The invention will now be described with reference to the schematic drawing, wherein FIG. 1 is a side view of separating apparatus, FIG. 2 is a front view of the left end of the separating apparatus illustrated in FIG. 1, FIG. 3 is a longitudinal section through the separating apparatus illustrated in FIG. 1 submerged in a flowing liquid, FIG. 4 is a side view of another embodiment, FIG. 5 is a front view of the left end of the embodiment illustrated in FIG. 4, FIG. 6 is a side view of still another embodiment, and FIG. 7 is a front view of the left end of the embodiment illustrated in FIG. 6.

DETAILED DESCRIPTIONS OF THE PREFERRED EMBODIMENTS

FIGS. 1 through 3 illustrate apparatus for separating particles suspended in a flowing liquid to obtain a clean sample current, one, that is, with few or no particles suspended in it. The separating apparatus is primarily constituted of a body 1 in the form of a surface of rotation with its axis 3 paralleling the current.

The interior 4 of body 1 is empty. The upstream end 5 of the body is connected to its downstream end 6 by an essentially smooth shaft 7. Mounted around the section of shaft just upstream of the body's downstream end 6 are several baffles 8 distributed parallel with the axis 3 of rotation of body 1. Baffles 8 are shaped like skirts and taper in radially from their outer edge toward the upstream end 5 of body 1. In the gap between each adjacent pair of baffles 8 are intakes 9 in the shaft into the interior 4 of body 1.

The upstream end 5 of body 1 is approximately hemispherical and its downstream end 6 is flat. As will be evident from FIG. 3, the interior 4 of the body communicates with at least one connection 10 for liquid to exit or be extracted through and another connection 11 for an unillustrated line leading to a flushing device.

Extending out of the outer surface of the body 1 in the embodiment of the separating apparatus illustrated in FIGS. 4 and 5 are stabilizers in the form of a keel 12 and lateral horizontal flukes 13. These structures help to position the body in the current.

Body 1 also has a suspension rack 14 with several points 15 of attachment distributed along it. The body can be secured to buoys 17 or similar structures by lines attached to the points. The multiplicity of points makes it possible to ideally position the body within the flow of liquid in accordance with prevailing conditions with its axis 3 of rotation remaining horizontal and at least approximately parallel with the direction 2 of flow.

The body 1 in the embodiment illustrated in FIGS. 6 and 7 is secured to and preferably suspended from a structure 18 floating on the surface of the liquid. Floating structure 18 can also be exploited to precisely position body 1 and will keep it at the appropriate level even when the liquid temporarily stops flowing.

How the separating apparatus operates will now be specified with reference to FIG. 3. The stacked arrows at the left represent a dense suspension 19 of solid particles flowing in a direction 2 represented by the arrows aligned paralleling the axis 3 of rotation of body 1. The current initially clings to the surface of shaft 7 until it arrives at the first in the series of baffles 8. The baffle deflects the current radially away from body 1. As the liquid flows across baffles 8, most of the heavy and inert solid particles will be catapulted on, but the turbulence in the vicinity of the baffles will divert some of the liquid, composed as it is of lighter-weight molecules and entraining few or no particles, in between the baffles and into the interior 4 of body 1 through intakes 9. The continuously entering current component 20 with few or no particles suspended in it can either be analyzed while it is still inside body 1 or pumped out and up through liquid exit-or-extraction connection 10 and analyzed outside the system. It is also possible to filter more particles out of the liquid before it leaves interior 4.

I claim:

1. An apparatus for separating particles suspended in a flowing liquid for cleaning a current component, comprising a hollow body having an upstream end and a downstream end;

the upstream end of the body is closed and shaped substantially hemispherical;

the downstream end of the body is closed;

an essentially smooth, substantially cylindrical shaft connecting the upstream end of the body to the downstream end and having a longitudinal axis;

the downstream end of the body is surrounded by a series of baffles having a gap between each baffle;

intakes in said gaps between said baffles in the shaft for guiding said current component into the interior of the body;

at least one outlet for the liquid of said current component to be removed through;

means for suspending the body in the flowing liquid such that the body is submerged below a surface of the flowing liquid and such that its longitudinal axis is substantially parallel with the direction of flow of the flowing liquid.

2. The apparatus of claim 1, wherein the baffles are shaped like skirts extending all around the body.

3. The apparatus according to claim 1, wherein each said baffle includes an outer free edge, and the baffles taper radially in toward the upstream end of the body from their outer free edge.

4. The apparatus of claim 1, wherein the downstream end of the body is flat.

5. The apparatus of claim 1, wherein the body has a connection to a flushing device.

6. The apparatus of claim 1, wherein the body has stabilizing means to position it in the current.

7. The apparatus according to claim 1, wherein said means for suspending includes a suspension rack.

8. The apparatus of claim 7, wherein the suspension rack has several points of attachment distributed along it.

9. The apparatus of claim 1, wherein said means for suspending includes a floating device.

* * * * *